(12) United States Patent
Eckert et al.

(10) Patent No.: US 10,466,151 B2
(45) Date of Patent: Nov. 5, 2019

(54) METHOD FOR MEASURING DENSITY OF A FLUID

(71) Applicant: Endress + Hauser Flowtec AG, Reinach (CH)

(72) Inventors: Gerhard Eckert, Grenzach-Wyhlen (DE); Alfred Rieder, Landshut (DE); Hao Zhu, Freising (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 203 days.

(21) Appl. No.: 15/540,046

(22) PCT Filed: Nov. 18, 2015

(86) PCT No.: PCT/EP2015/076928
§ 371 (c)(1),
(2) Date: Jun. 27, 2017

(87) PCT Pub. No.: WO2016/107693
PCT Pub. Date: Jul. 7, 2016

(65) Prior Publication Data
US 2017/0356833 A1    Dec. 14, 2017

(30) Foreign Application Priority Data

Dec. 30, 2014   (DE) ........................ 10 2014 019 396
Jun. 18, 2015   (DE) ........................ 10 2015 109 744

(51) Int. Cl.
*G01N 9/00*          (2006.01)
*G01N 11/04*         (2006.01)
(Continued)

(52) U.S. Cl.
CPC ........... *G01N 9/002* (2013.01); *G01F 1/8431* (2013.01); *G01F 1/8436* (2013.01);
(Continued)

(58) Field of Classification Search
CPC .. G01N 9/002; G01N 2009/006; G01N 11/04; G01N 11/16; G01F 1/8477; G01F 1/8472; G01F 1/8436; G01F 1/8431
See application file for complete search history.

(56) References Cited

U.S. PATENT DOCUMENTS

| | | | |
|---|---|---|---|
| 5,027,662 A * | 7/1991 | Titlow | ............... G01F 1/8413 |
| | | | 73/861.356 |
| 2007/0219650 A1* | 9/2007 | Wang | .................. G01F 1/6847 |
| | | | 700/73 |

(Continued)

FOREIGN PATENT DOCUMENTS

| | | |
|---|---|---|
| CN | 1145473 A | 3/1997 |
| CN | 101858764 A | 10/2010 |

(Continued)

OTHER PUBLICATIONS

International Search Report, EPO, The Netherlands, dated Feb. 26, 2016.

(Continued)

*Primary Examiner* — Blake A Tankersley
(74) *Attorney, Agent, or Firm* — Bacon & Thomas, PLLC (57) ABSTRACT

A method is provided for measuring density of a fluid by means of at least one at least sectionally curved measuring tube. The measuring tube is adapted to be flowed through by the fluid and concurrently to be caused to vibrate over a wanted oscillatory length, namely a tube length measured from a first tube end to a second tube end, a length which is greater than a minimum separation of the second tube end from the first tube end. According to the invention, among other things, also a tilt measured value representing an inclination of the at least one measuring tube in the static resting position relative to a local acceleration of gravity is ascertained, in such a manner that such represents an angle of intersection between a direction vector of an imaginary (Continued)

first reference axis (y-axis) and a direction vector of an imaginary second reference axis (g-axis). The first reference axis is so selected that it is perpendicular to an imaginary third reference axis (z-axis) imaginarily connecting the first tube end and the second tube end and points in the direction of a peak of the at least one measuring tube farthest from the third reference axis in the static resting position, while the second reference axis is so selected that it extends through a shared intersection of the first and third reference axes and points in the vertical direction, namely in the direction of the local acceleration of gravity. The tilt measured value is used together with a parameter measured value representing an oscillation frequency of the at least one measuring tube for ascertaining at least one density measured value representing the density of the fluid.

39 Claims, 6 Drawing Sheets

(51) Int. Cl.
*G01N 11/16* (2006.01)
*G01F 1/84* (2006.01)

(52) U.S. Cl.
CPC .......... *G01F 1/8472* (2013.01); *G01F 1/8477* (2013.01); *G01N 11/04* (2013.01); *G01N 11/16* (2013.01); *G01N 2009/006* (2013.01)

(56) References Cited

U.S. PATENT DOCUMENTS

| 2008/0229846 A1 | 9/2008 | Grotzer | |
| 2011/0016990 A1* | 1/2011 | Huber | G01F 1/8427 73/861.357 |
| 2014/0060154 A1 | 3/2014 | Dijk | |

FOREIGN PATENT DOCUMENTS

| CN | 102686985 A | 9/2012 |
| CN | 104105955 A | 10/2014 |
| DE | 102014019396 A1 | 6/2016 |
| WO | 2016107693 A1 | 7/2016 |

OTHER PUBLICATIONS

English Translation of the International Preliminary Report on Patentability, WIPO, Geneva, CH, dated Jul. 13, 2017.
Chinese Office Action in corresponding Chinese Application No. 201580071878.7, dated Feb. 20, 2019.

* cited by examiner

METHOD FOR MEASURING DENSITY OF A FLUID

The invention relates to a method for measuring density of a fluid by means of at least one at least sectionally curved measuring tube, which is adapted to be flowed through by such fluid and concurrently to be caused to vibrate.

Described in US-A 2008/0229846 and US-A 20140060154 are measuring systems for measuring at least one measured variable of a flowing fluid. These measuring systems comprise a measuring transducer flowed-through during operation by fluid to be measured as well as an electronics electrically coupled with the measuring transducer. During operation, the measuring transducer registers at least one measured variable of the fluid and delivers at least one measurement signal corresponding to the measured variable, and the measuring device-electronics, by means of the at least one measurement signal, generates at least one measured value quantitatively representing the at least one measured variable. The measured variable to be registered can be a viscosity, density or mass flow rate of the fluid. For conveying fluid to be measured, the measuring transducer includes at least one measuring tube, which is curved, at least sectionally, for example, essentially U- or V-shaped, and which is, especially, adapted to be flowed through by fluid to be measured and concurrently to be caused to vibrate, in such a manner that the at least one measuring tube executes, at least partially, wanted oscillations, for example, bending oscillations, with a wanted oscillation frequency dependent on the density of the fluid. By means of at least one oscillation sensor, corresponding oscillatory movements of the at least one measuring tube are pointwise registered and converted into at least one oscillation signal representing at least oscillations of the at least one measuring tube, in such a manner that the oscillation signal has a signal parameter appropriately corresponding with the wanted oscillation frequency. Using the at least one oscillation signal, additionally at least one parameter measured value is ascertained for the signal parameter, in such a manner that the parameter measured value represents the wanted oscillation frequency of the at least one measuring tube and, based on the parameter measured value, at least one measured value quantitatively representing the measured variable is ascertained.

The measuring system described in US-A 2008/0229846 is additionally adapted to execute a method, in the case of which, for compensation of measurement errors accompanying an installed position of the measuring transducer and/or for validation of the at least one measured value, an inclination of the measuring transducer, namely an inclination of at least one principle axis of inertia of the measuring transducer perpendicular, for example, also essentially perpendicular, to an imaginary flow axis of the measuring transducer is ascertained relative to at least one imaginary reference axis (g-axis) and, derived therefrom a measured value of inclination is determined, which quantifies a deviation of the ascertained inclination from the predetermined reference value. Said measured value of inclination is thereafter used, in order together with the previously indicated parameter measured value to ascertain, in a manner not specified in greater detail, at least one measured value for one of the previously indicated, measured variables. For registering, or also monitoring, the inclination of the measuring transducer, the measuring system can have an inclination sensor. Selected as reference axis (g-axis) is an imaginary fall line pointing in the direction of the acceleration of gravity, consequently in the vertical direction.

Starting from the above indicated state of the art, an object of the invention is to provide an improved method, in the case of which, especially also in the case of measuring the density of fluids by means of an at least sectionally curved measuring tube, especially one curved in U- or V-shape, equally as well one flowed through by the fluid and concurrently caused to vibrate, measuring errors at times occurring, especially measuring errors dependent on the installed position of the measuring tube, can be further lessened, or in the case of which an accuracy of density measurement further improved compared with the method known from the state of the art can be achieved.

For achieving the object, the invention resides in a method for measuring density of a fluid, for example, a fluid flowing at least at times, by means of at least one at least sectionally curved, measuring tube, for example, a U- or V-shaped, measuring tube, which is adapted to be flowed through by the fluid and concurrently to be caused to vibrate over a wanted oscillatory length, namely a tube length measured from a first tube end to a second tube end, which length is greater than a minimum separation of the second tube end from the first tube end. The method of the invention comprises, among other things, ascertaining a tilt measured value, namely a measured value for an inclination of the at least one measuring tube in static resting position relative to a local acceleration of gravity, in such a manner that the tilt measured value represents an angle of intersection between a direction vector of an imaginary first reference axis (y-axis) and a direction vector of an imaginary second reference axis (g-axis), for example, corresponds to a numerical value related to angular degrees for the angle of intersection or a numerical value for a cosine of the angle of intersection. The first reference axis is so selected that it is perpendicular to an imaginary third reference axis (z-axis) imaginarily connecting the first tube end and the second tube end, and points in the direction of a peak of the at least one measuring tube farthest from the third reference axis in the static resting position, while the second reference axis is so selected that it extends through an intersection of the first and third reference axes and points in the vertical direction, namely in the direction of the local acceleration of gravity. The method of the invention comprises, furthermore, permitting fluid to flow through the at least one measuring tube and causing the measuring tube to vibrate, in such a manner that the at least one measuring tube executes, at least partially, wanted oscillations, for example, bending oscillations, with a wanted oscillation frequency dependent on the density of the fluid, as well as producing at least one oscillation signal representing at least oscillations of the at least one measuring tube, in such a manner that the oscillation signal has at least one signal parameter corresponding to the wanted oscillation frequency, for example, namely a signal frequency corresponding to the wanted oscillation frequency.

Moreover, the method of the invention comprises using the at least one oscillation signal for ascertaining at least one parameter measured value for the signal parameter, in such a manner that the parameter measured value represents the wanted oscillation frequency, $f_N$, of the at least one measuring tube as well as using both the at least one parameter measured value as well as also the tilt measured value for ascertaining at least one density measured value representing the density of the fluid.

In a first embodiment of the invention, it is, furthermore, provided that the ascertaining of the density measured value comprises ascertaining a cosine of the angle of intersection.

In a second embodiment of the invention, it is, furthermore, provided that the ascertaining of the density measured value comprises ascertaining a square of the wanted oscillation frequency of the at least one measuring tube.

In a third embodiment of the invention, it is, furthermore, provided that the ascertaining of the density measured value comprises using the at least one parameter measured value for ascertaining a square of the wanted oscillation frequency of the at least one measuring tube.

In a fourth embodiment of the invention, it is, furthermore, provided that the ascertaining of the tilt measured value comprises measuring the angle of intersection, for example, in angular degrees.

In a fifth embodiment of the invention, it is, furthermore, provided that the ascertaining of the tilt measured value comprises ascertaining a cosine of the angle of intersection.

In a sixth embodiment of the invention, it is, furthermore, provided that the tilt measured value corresponds, for example, to a numerical value for the angle of intersection related to angular degrees.

In a seventh embodiment of the invention, it is, furthermore, provided that the tilt measured value corresponds to a numerical value for a cosine of the angle of intersection.

In an eighth embodiment of the invention, it is, furthermore, provided that the ascertaining of the tilt measured value and the permitting of fluid to flow through the at least one measuring tube occur at the same time.

In a ninth embodiment of the invention, it is, furthermore, provided that the ascertaining of the tilt measured value and the causing of the at least one measuring tube to vibrate occur at the same time.

In a tenth embodiment of the invention, it is, furthermore, provided that on the at least one measuring tube a component, for example, a coil or a permanent magnet of an electro-mechanical, for example, electro-dynamic, oscillation exciter useful for active exciting of oscillations of the measuring tube, is placed, in such a manner that the imaginary first reference axis, or a lengthening thereof, imaginarily intersects the oscillation exciter, or the component of the oscillation exciter.

In an eleventh embodiment of the invention, it is, furthermore, provided that the at least one measuring tube has only two oscillation nodes, of which a first oscillation node is located in the first tube end and a second oscillation node is located in the second tube end, and, consequently the at least one measuring tube has a bending oscillation fundamental mode having a single oscillatory antinode. Developing this embodiment of the invention further, it is, additionally, provided that the wanted oscillations are so embodied that they correspond to oscillations of the at least one measuring tube in the bending oscillation fundamental mode.

In a twelfth embodiment of the invention, it is, furthermore, provided that the ascertaining of the at least one density measured value comprises use both of the at least one parameter measured value as well as also the tilt measured value for ascertaining a tilt-correction value, in such a manner that the tilt-correction value represents a dependence of the signal parameter both on the inclination of the at least one measuring tube, especially namely on a cosine of the angle of intersection, as well as also on a total-weight of the measuring tube with fluid located therein. Developing this embodiment of the invention further, it is, additionally, provided that the ascertaining of the tilt-correction value comprises ascertaining a square of the wanted oscillation frequency of the at least one measuring tube, for example, with application of the at least one parameter measured value, and/or ascertaining a fourth power of the wanted oscillation frequency of the at least one measuring tube, for example, with application of the at least one parameter measured value. Alternatively or supplementally, the ascertaining of the tilt-correction value can also comprise ascertaining a provisional density measured value, which represents, interim, the density of the fluid, for example, in such a manner that the provisional density measured value in the case of an angle of intersection of 0° represents density, which is less than the density of the fluid and/or that the provisional density measured value in the case of an angle of intersection of 180° represents density, which is greater than the density of the fluid and/or that the provisional density measured value and the density measured value are equal in the case of an angle of intersection of 90°. With application of the tilt correction value, the ascertaining of the density measured value can, for example, occur in that, first of all, a square of the wanted oscillation frequency of the at least one measuring tube is ascertained and thereafter reduced by the tilt correction value. Furthermore, the tilt correction value can be stored in a data memory, for example, a non-volatile data memory, for instance, in order, for ascertaining the density measured value, to be able to read the tilt correction value from the data memory.

In a first further development of the method of the invention, such further comprises bringing the at least one measuring tube into a static resting position, for example, in such a manner that the angle of intersection is greater than 0° and/or less than 180°.

In a second further development of the method of the invention, such further comprises storing the tilt measured value in a data memory, for example, a non-volatile data memory. The use of the tilt measured value for ascertaining the density measured value can then, for example, also comprise a read-out of the tilt measured value from the data memory.

In a third further development of the method of the invention, such further comprises using an inclination sensor, for example, an inclination sensor held durably in a fixed positional relationship relative to the at least one measuring tube, consequently relative to the first and third reference axes and/or a uniaxial inclination sensor, namely one having exactly one measurement axis, for ascertaining the tilt measured value. The inclination sensor can, for example, be so arranged that a measurement axis is parallel to the first reference axis (y-axis), or coincides with the first reference axis. Furthermore, the inclination sensor can also have two or more measurement axes perpendicular to one another.

A basic idea of the invention is, in the case of ascertaining density, to take into consideration a deformation of the at least one measuring tube resulting from a force of gravity acting on the at least one measuring tube, or to take into consideration an influencing of the oscillation characteristics of the at least one measuring tube, not least of all also its resonant frequencies, associated with such deformation. Although such deformations, even in the case of curved measuring tubes, are rather small, it could nevertheless be detected that the measuring errors resulting therefrom can be quite significant, so that, for the purpose of assuring an, at times, required, extremely high accuracy of measurement of over 99.9% (measuring errors<0.1%) for the density measurement, they should be appropriately corrected. Surprisingly, it has, in such case, furthermore, been found that the extent of the influencing of the oscillation characteristics of the at least one measuring tube by the force of gravity is sufficiently exactly quantifiable by measurement of the inclination of the above mentioned y-axis relative to the vertical direction (g-axis), so that the above mentioned measuring error is determinable and accordingly correctable by ascertaining the inclination of the y-axis relative to the vertical direction (g-axis).

The invention as well as advantageous embodiments thereof will now be explained in greater detail based on examples of embodiments, which are shown in the figures of the drawing. Equal, or equally acting or equally functioning, parts are provided in all figures with equal reference characters; when perspicuity requires or it otherwise appears sensible, already used reference characters are omitted in subsequent figures. Other advantageous embodiments or further developments, especially also combinations, of first only individually explained aspects of the invention, will become evident, furthermore, from the figures of the drawing and/or from claims per se.

Figure 1:
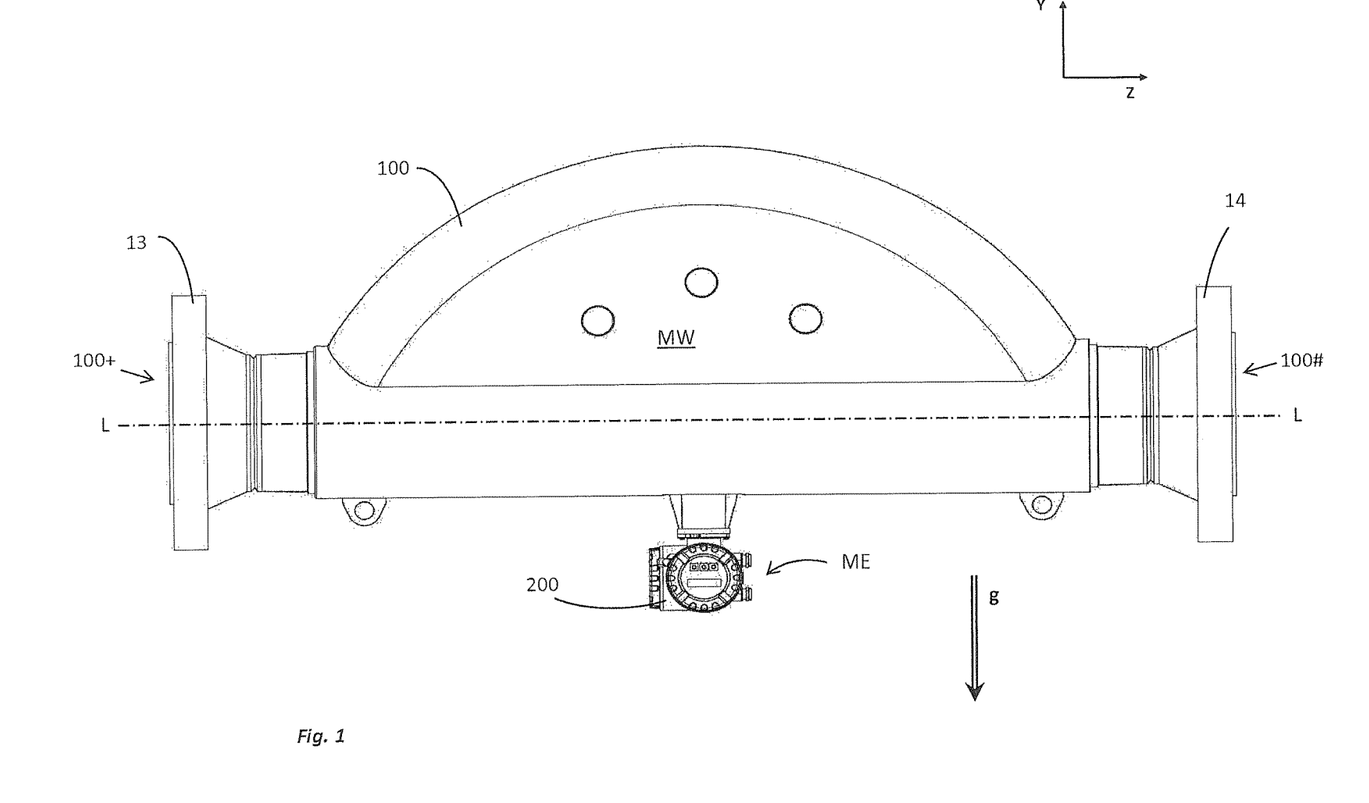
FIG. 1 in a planar side view, in a horizontal installed position, a measuring system suitable for measuring density.
Figure 2:
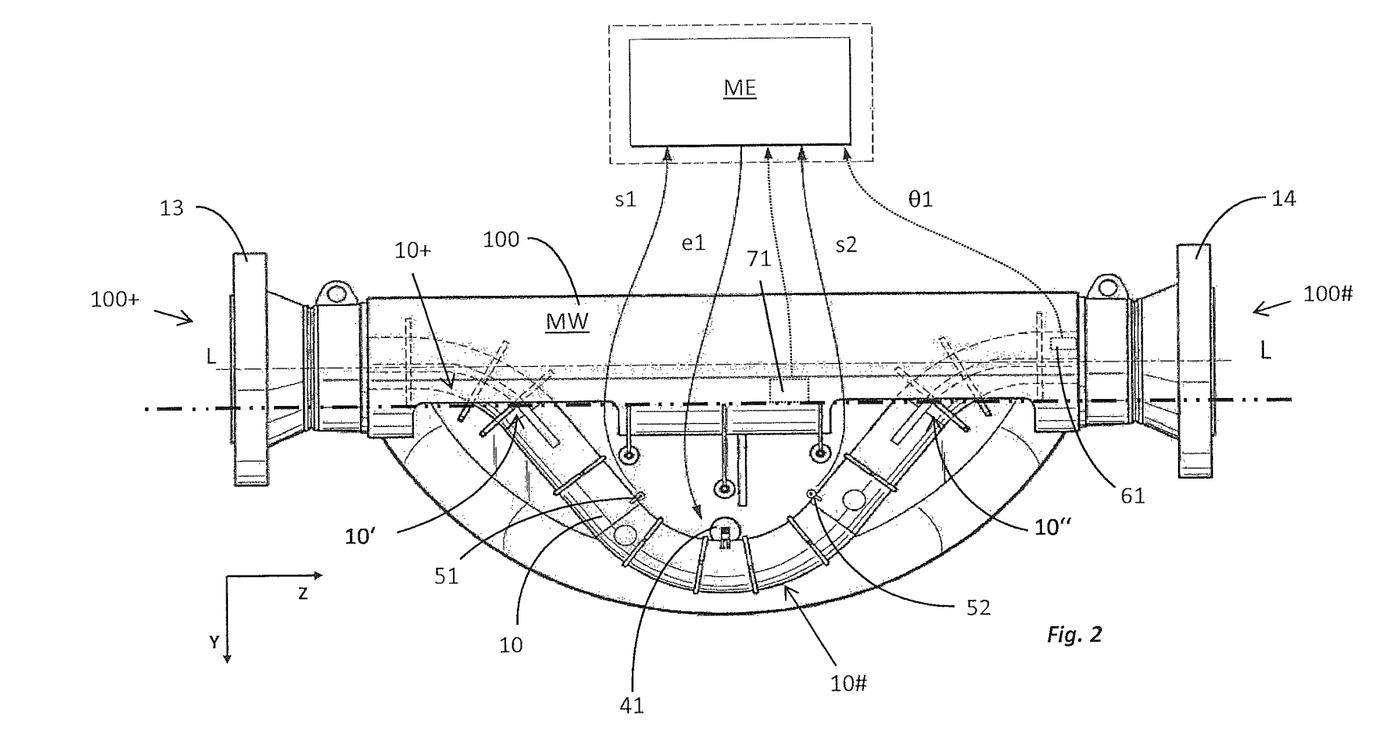
FIG. 2 a measuring system of FIG. 1 with a measuring transducer illustrated in a partially sectioned, planar, side view.
Figure 3:
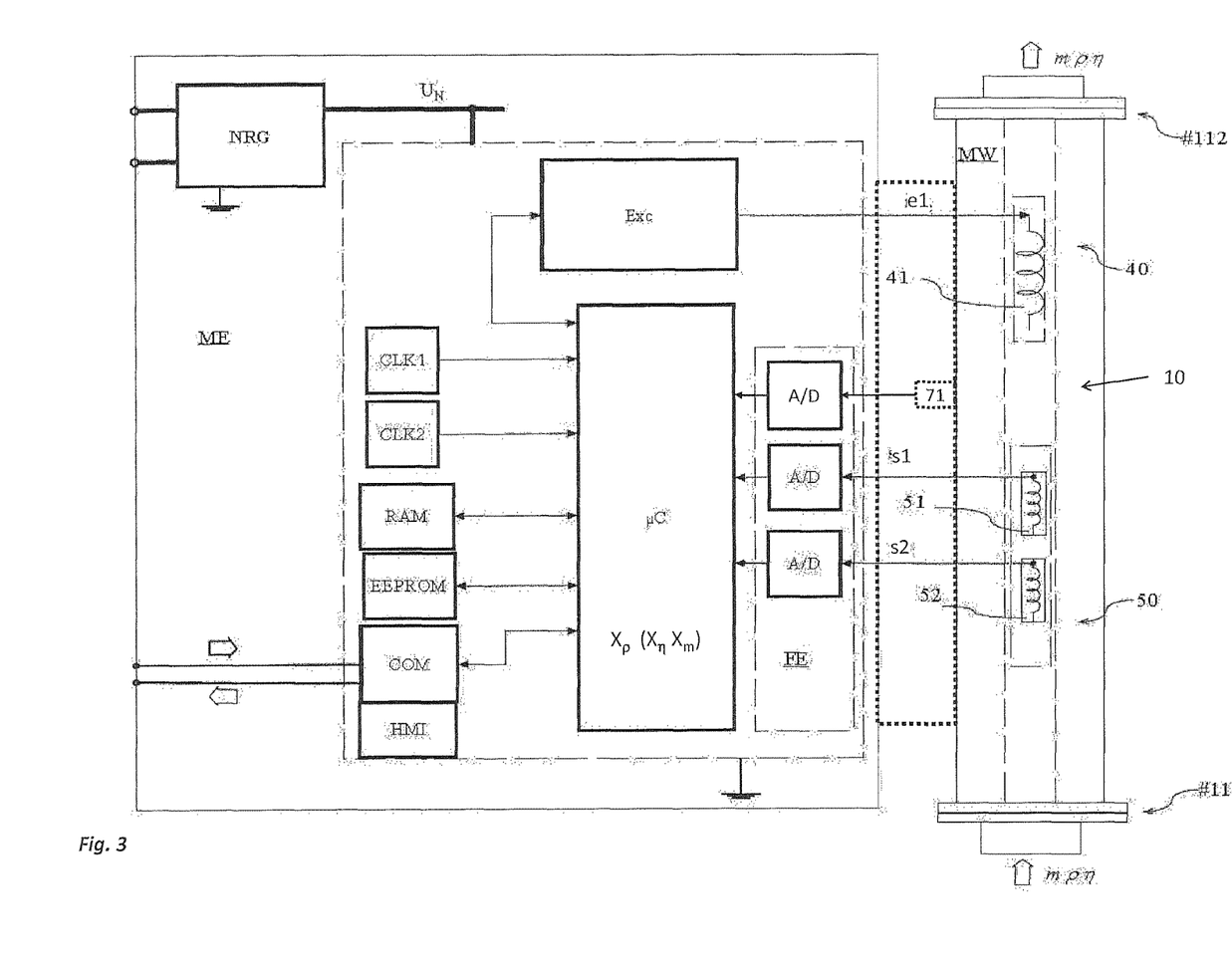
FIG. 3 a measuring system of FIG. 1 with an electronics illustrated schematically in the manner of a block diagram.

Schematically shown in FIGS. 1, 2, and 3 is a measuring system especially suitable for application in industrial measuring—and automation technology and serving for measuring density ρ of a flowable (consequently guidable in a line, such as, for instance, a pipeline or a flume) fluid FL, for example, thus a liquid, a gas or a dispersion, namely a measuring system for producing a large number of density-measured values $X_\rho$ sequentially representing the density as a function of time. The measuring system is implemented as an in-line-measuring device, namely a measuring system insertable into the course of a pipeline (not shown). The measuring system can, accordingly, for example, also be a Coriolis mass flow/density measuring device measuring supplementally to density ρ also a mass flow rate ṁ of flowing fluids and/or a density/viscosity measuring device measuring supplementally to density also a viscosity η of flowing fluids.

For registering the density, the measuring system comprises a measuring transducer MT of vibration-type insertable into the course of a pipeline (not shown). During operation, fluid to be measured flows through the measuring transducer, which has at least one oscillatably held, at least sectionally curved, measuring tube 10, for example, a measuring tube curved with U- or V-shape. As directly evident from a combination of FIGS. 1, 2 and 3, the measuring transducer is electrically connected to an electronics ME accommodated in an electronics-housing 200 and lastly delivering the density measured values $X_\rho$.

Figure 4:
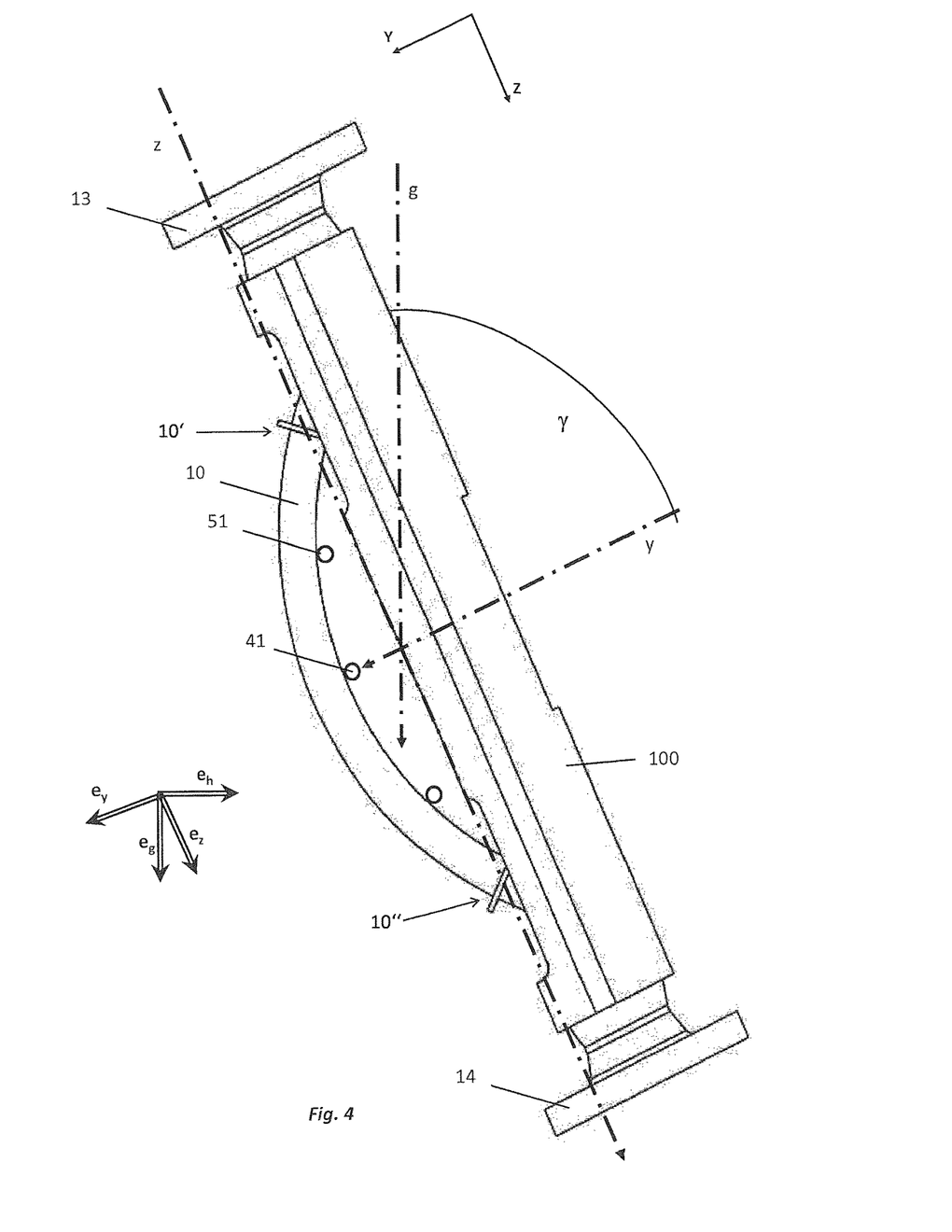
FIG. 4 schematically in a planar, partially sectioned, side view, in a first inclined installed position, a measuring transducer suitable for a measuring system of FIG. 1.
Figure 5:
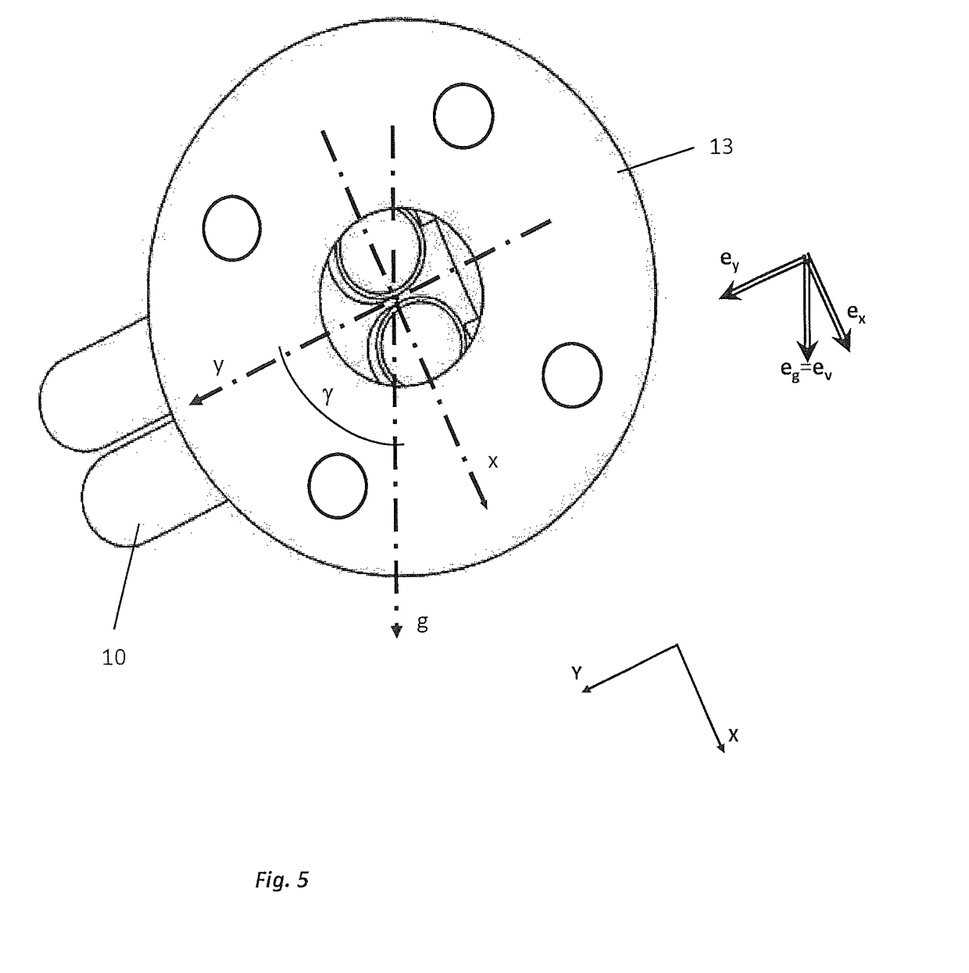
FIG. 5 schematically in a planar, partially sectioned, side view, in a second inclined installed position, a measuring transducer suitable for a measuring system of FIG. 1.
Figure 6:
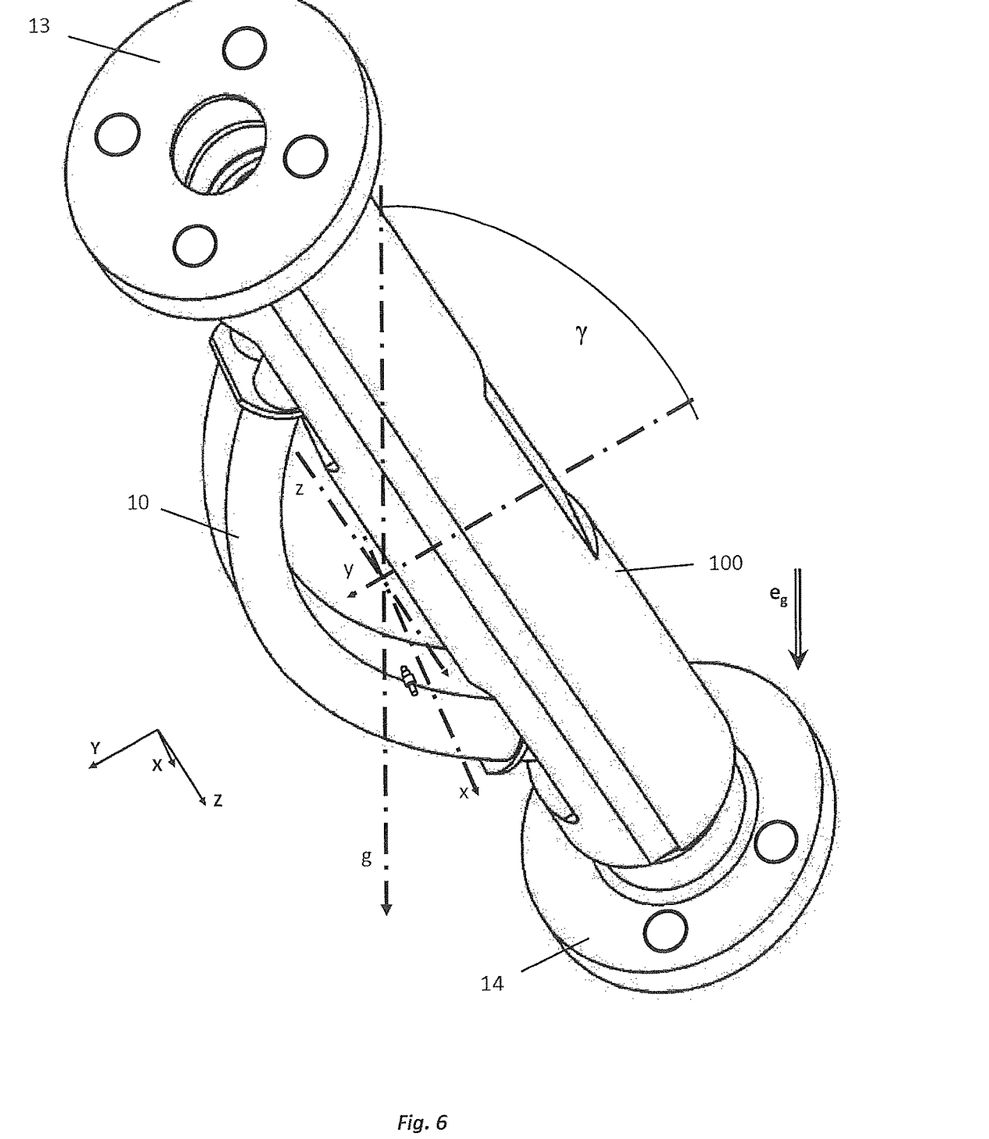
FIG. 6 schematically in a planar, partially sectioned, side view, in a third inclined installed position, a measuring transducer suitable for a measuring system of FIG. 1.

As shown schematically in FIG. 2 and directly evident from a combination of FIGS. 1, 2 and 3, the at least one measuring tube 10 can, for example, also be accommodated in a measuring transducer-housing 100. For the typical case for such a measuring transducer of vibration-type, in which case the measuring transducer, especially its at least one measuring tube, is to be assembled releasably with the process line, for example, a process line in the form of a metal pipeline, there are provided, such as indicated in FIGS. 1, 2 and 3, and also FIGS. 4, 5, and 6, and directly evident from their combination, at the inlet end (100+) of the measuring transducer a first connecting flange 13 for connection to a line segment of the process line supplying fluid to the measuring transducer and at the outlet end (100#) a second connecting flange 14 for connection to a line segment of the process line removing fluid from the measuring transducer. The connecting flanges 13, 14 can, in such case, such as quite usual in the case of measuring transducers of the described type, also be integrated terminally in the above mentioned measuring transducer housing 100, consequently form an inlet-end measuring transducer end 100+, respectively an outlet-end measuring transducer end 100#.

The at least one measuring tube 10 has a lumen surrounded by a tube wall, for example, a metal tube wall, and is, especially, adapted to guide in its lumen a volume portion of the fluid FL, especially to be flowed through by the fluid FL, and, concurrently, to be caused to vibrate over a wanted oscillatory length, namely a tube length measured from a first tube end 10' to a second tube end 10", which (for reasons of the selected tube form) is greater than a minimum separation of the second tube end from the first tube end 10', and, indeed, in such a manner that the measuring tube 10 guiding the fluid executes, at least partially, wanted oscillations, namely mechanical oscillations with a wanted oscillation frequency $f_N$, namely a wanted oscillation frequency dependent on the density, consequently a wanted oscillation frequency useful as a measure for the density, especially in such a manner that the at least one measuring tube oscillates about a static resting position.

The wanted oscillatory length of the at least one measuring tube corresponds, in such case, to a stretched length of a tube segment of the at least one measuring tube extending between the first tube end 10' and the second tube end 10", respectively a length of an imaginary directrix extending within its lumen for an imaginary family of spheres for forming a channel—, and tube surface, enveloping the lumen. The wanted oscillation frequency $f_N$ can be, for example, an oscillation frequency corresponding to a resonant frequency $f_r$, or a frequency dependent on such a resonant frequency, of the at least one measuring tube, or of the measuring transducer formed therewith.

Naturally, the measuring tube 10 has a large number of different oscillation modes, not least of all also a bending oscillation fundamental mode having only two oscillation nodes, of which a first oscillation node is located toward the first tube end and a second oscillation node is located toward the second tube end, and, consequently, a single oscillatory antinode. In the bending oscillation fundamental mode, the at least one measuring tube 10 is deflected (in the manner of a unilaterally clamped cantilever) about an imaginary oscillation axis imaginarily connecting the two pipe ends 10', 10" with one another—here an imaginary oscillation axis additionally essentially parallel to an imaginary longitudinal axis L of the measuring transducer. In an additional embodiment of the invention, selected as wanted oscillations are oscillations of the at least one measuring tube in exactly this bending oscillation fundamental mode, so that there serves as wanted oscillation frequency $f_N$ an oscillation frequency corresponding to an eigenfrequency of the bending oscillation fundamental mode.

The measuring transducer is, furthermore, adapted, based on the mechanical oscillations of the measuring tube 10, to generate at least one oscillation signal s1 representing at least oscillations of the at least one measuring tube, in such a manner that the oscillation signal s1 has in the case of excited wanted oscillations at least one signal parameter corresponding to the wanted oscillation frequency $f_N$, for example, namely a signal frequency $f_1$ corresponding to the wanted oscillation frequency $f_N$.

For implementing the invention, besides the measuring transducers proposed in the examples of embodiments and as shown in FIGS. 2 and 4, 5, or 6, for example, also such measuring transducers can serve, such as are proposed in, among others, the above cited US-A 2010/0236338, US-A 2010/0242623, US-A 2010/0242624, U.S. Pat. No. 5,602,345, 5,796,011, 6,513,393, 6,840,109, 6,920,798 or U.S. Pat. No. 7,017,424, 7,360,451 or 6,666,098, or such as commercially available from the applicant under the designations "PROMASS E", "PROMASS F", "PROMASS H", "PROMASS P" or "PROMASS S" for measuring both density as well as also mass flow rate, or total mass flow, of flowing fluids. In accordance therewith, the measuring transducer can, supplementally to the measuring tube 10, have, for example, at least one further measuring tube, especially a measuring tube equally constructed and/or parallel to measuring tube 10, so that the measuring transducer can also be formed by means of two or more measuring tubes. The at least two measuring tubes can by means of an inlet-end flow divider and an outlet-end flow divider, in given cases, supplementally also by means of in- and outlet-end coupling elements, be mechanically coupled with one another and, during operation, caused to vibrate, at least at times, for producing the at least one oscillation measurement signal, for instance, with equal frequency of a shared oscillation frequency, however, opposite-equally relative to one another, thus phase shifted by 180 degrees relative to one another For active exciting of vibrations of the at least measuring tube 10, especially also the wanted oscillations required for measuring the density, the measuring transducer MT can, furthermore, have at least one electro-mechanical, for example, electrodynamic, oscillation exciter 41 connected with the at least one measuring tube 10 and formed by means of plunging armature and coil. The oscillation exciter serves, in such case, especially, to convert an electrical excitation power fed by means of at least one electrical driver signal e1 into, e.g. pulsating or harmonic, namely essentially sinusoidal, exciter forces, which act correspondingly on the measuring tube 10 and, thus, actively excite the desired wanted oscillations. The oscillation exciter can, for example, be so embodied and arranged that it —, as well as also shown in FIG. 2 and quite usual in the case of measuring transducers of the type being discussed—acts in the region of a peak of the at least one measuring tube on the measuring tube, so that the exciter forces produced therewith are introduced into the measuring tube in the region of the peak of the measuring tube. The above mentioned driver signal can, as indicated in FIG. 3, be provided, for example, by means of a driver-circuit Exc provided in the electronics ME. The exciter forces generated by converting electrical excitation power fed from the at least one oscillation exciter 41 can, in manner known per se to those skilled in the art, be correspondingly adjusted by means of the previously indicated driver circuit Exc, for instance, as regards their magnitude, by means of an electrical current controller implemented in the driver circuit and controlling an amplitude (electrical current level) of an electrical current of the driver signal and/or by means of a voltage controller controlling an amplitude (voltage level) of a voltage of the driver signal and, as regards their instantaneous frequency, e.g. by means of an phase locked loop (PLL) implemented in the driver circuit Exc. Compare, for this, for example, also U.S. Pat. No. 4,801,897 or 6,311,136. The construction and the application of phase locked loops for the active exciting of measuring tubes to a certain wanted frequency is described at length e.g. in U.S. Pat. No. 4,801,897. Of course, also other driver circuits suitable for adjusting the exciter energy and known, per se, to those skilled in the art can be used, for example, also one of those of the above discussed state of the art, for instance, as described in U.S. Pat. No. 4,777,833, 4,801,897, 4,879,911, 5,009,109, 5,024,104, 5,050,439, 5,804,741, 5,869,770, 6,073,495, or 6,311,136. Furthermore, reference is made, as regards an application of such driver circuits, to the electronics provided with measurement transmitters of the series "PROMASS 83", such as commercially available from the applicant, for example, also in connection with measuring transducers of the series, "PROMASS E", "PROMASS F", "PROMASS H", "PROMASS P", and "PROMASS S" also serving for measuring density. Their driver circuit is, for example, in each case, additionally also so executed that wanted oscillations can be controlled to a constant amplitude, thus an amplitude also largely independent of the density ρ and also the viscosity η of the particular fluid to be measured.

For producing the oscillation signal s1, the measuring transducer includes, according to an additional embodiment of the invention, at least one oscillation sensor 51, for example, an electrodynamic oscillation sensor, which is adapted to register oscillatory movements of the at least one measuring tube and to transduce such into the oscillation signal s1. The oscillation signal s1 can, for example, be an electrical, alternating voltage. The oscillation sensor 51 can, such as quite usual for measuring transducers of the type being discussed, be arranged outwardly on the at least one measuring tube spaced from the at least one oscillation exciter 41 and be adapted to deliver the oscillation measurement signal s1 in the form of an electrical (alternating-) voltage corresponding to the oscillations with an amplitude (voltage level) dependent on a velocity of the oscillations of the measuring tube and a frequency corresponding to the wanted frequency $f_N$. In the case of its application in a Coriolis mass flow measuring device, the measuring transducer can, furthermore, have a second oscillation sensor 52 spaced in the flow direction from the first oscillation sensor 51, wherein the first oscillation sensor can be placed, for example, on the inlet end of the at least one measuring tube, while the second oscillation sensor is arranged downstream of the first oscillation sensor at the outlet end of the at least one measuring tube. Moreover, the measuring transducer can have, for example, also at least one temperature sensor 61 thermally coupled with the at least one measuring tube, for example, adhered thereon, for producing a temperature measurement signal θ1 useful for correcting temperature influences on the wanted oscillations, and on the at least one oscillation signal s1.

The at least one oscillation signal s1 of the measuring transducer is further processed in the electronics ME, which is, among other things, so adapted, with application at least of the at least one oscillation signal s1, to ascertain at least one parameter measured value $X_f$ for the above mentioned, at least one signal parameter corresponding to the wanted oscillation frequency $f_N$, in such a manner that the parameter measured value represents the wanted oscillation frequency $f_N$ of the at least one measuring tube, as well as, with application of the parameter measured value, also to ascertain the density measured value $X_ρ$ representing the density of the fluid. In the case of an application in a Coriolis mass flow measuring device, the electronics ME can, furthermore, also serve, with application of the oscillation measurement signals generated by the measuring transducer MT, namely based on a phase difference detected between the oscillation measurement signals s1, s2 of the first and second oscillation sensors 51, 52, and caused by Coriolis forces in the flowing fluid, recurringly to ascertain a mass flow measured value $X_m$, which represents a measured mass flow rate, $\dot{m}$, of the fluid guided through the measuring transducer. Alternatively thereto or in supplementation thereof, the measuring—and evaluating circuit can, such as quite usual in the case of measuring systems of the type being discussed, in given cases, also be used to ascertain, based on the supplied electrical excitation power as well as the at least one oscillation measurement signal s1, a viscosity-measured value $X_\eta$ representing a viscosity $\eta$ of the fluid; compare, for this, also the above referenced U.S. Pat. No. 7,284,449, 7,017,424, 6,910,366, 6,840,109, 5,576,500 or 6,651,513. For evaluation of the signals delivered by the measuring transducer, e.g. for generating the above mentioned measured values ($X_f$, $X_\rho$, . . . ), the electronics ME can have, as well as also shown schematically in FIG. 3, furthermore, a, measuring—and evaluating circuit µC formed, for example, by means of at least one microprocessor and/or by means of a digital signal processor (DSP). Each of the oscillation measurement signals generated by the measuring transducer can, in such case, also be, first of all, preprocessed, especially preamplified, filtered and digitized, by means of an input circuit FE likewise provided in the electronics ME and connected in front of the actual measuring—and evaluating circuit µC and thereafter be forwarded correspondingly to the measuring—and evaluating circuit µC in the form of a digital signal. The program code for such evaluating programs serving for generating measured values, not least of all also the density measured values, and for control programs serving for operating the measuring transducer can be stored e.g. persistently in a non-volatile data memory EEPROM of the electronics ME and in the case of start up of the electronics be loaded into a volatile data memory RAM, e.g. one integrated in the processor. Equally, measured values generated by means of the electronics ME during operation can be kept in such a volatile memory, in given cases, also the same volatile memory, or loaded into such a non-volatile data memory and correspondingly kept for later, further processing.

Measured values generated by means of the electronics ME, not least of all density measured values $X_\rho$, however, also, in given cases, mass flow measured values $X_m$, and/or viscosity measured values $X_\eta$, generated by means of the electronics ME, can, for example, also be displayed on-site. For visualizing measuring system internally produced measured values and/or, in given cases, measuring system internally generated system status reports, such as, for instance, an error report or an alarm, on-site, the measuring system can, as also indicated in FIG. 3, have, furthermore, a display- and interacting element HMI communicating with the electronics, in given cases, also a portable HMI, such as, for instance, an LCD-, OLED- or TFT-display placed in the electronics housing behind a window correspondingly provided therein, as well as a corresponding input keypad and/or a touch screen. In advantageous manner, the electronics ME, for example, also a remotely parameterable electronics ME, can, furthermore, be so designed that it can, during operation of the measuring system, exchange with an electronic data processing system superordinated thereto, for example, a programmable logic controller (PLC), a personal computer and/or a work station, via a data transmission system, for example, a fieldbus system and/or wirelessly per radio, measuring—and/or other operating data, such as, for instance, current measuring—and/or system diagnostic values or setting values serving for control of the measuring system. Furthermore, the electronics ME can be so designed that it can be fed from an external energy supply, for example, also via the aforementioned fieldbus system. For the case, in which the measuring system is provided for coupling to a fieldbus—or another communication system, the electronics ME, for example, also an on-site and/or via communication system (re-)programmable, electronics ME, can additionally have a corresponding communication interface for data communication, e.g. for sending measuring—and/or operating data, thus the measured values representing at least one measured variable, to the programmable logic controller or a superordinated process control system and/or for receiving settings data for measuring system. Particularly for the case, in which the measuring system is provided for coupling to a fieldbus—or another communication system, the electronics ME can, furthermore, have a communication interface COM embodied for data communication according to one of the relevant industry standards. Moreover, the electronics ME can, for example, have an internal energy supply circuit ESC, which is fed via the aforementioned fieldbus system during operation from an external energy supply provided in the aforementioned data processing system. In such case, the electronics can, furthermore, e.g. be so embodied that it is electrically connectable with the external electronic data processing system by means of a two-wire connection 2L, for example, one configured as a 4-20 mA electrical current loop, and that it is supplied thereby with electrical energy as well as being able to transmit measured values to the data processing system; the measuring system can, however, for example, also be embodied as a so-called four-conductor measuring device, in the case of which the internal energy supply circuit ESC of the electronics ME is connected by means of a first pair of lines with an external energy supply and the internal communication circuit COM of the electronics ME is connected by means of a second pair of lines with an external data processing circuit or an external data transmission system. The electronics ME can, furthermore, —, as well as also shown schematically—be accommodated in a corresponding electronics housing 200, for example, an impact— and/or also explosion resistant and/or hermetically sealed and/or modularly constructed, electronics housing. The electronics housing 200 can, for example, be arranged remotely from the measuring transducer or, such as shown in FIG. 1, for example, be externally affixed to the transducer housing 100, in order to form a single compact device directly on the measuring transducer MT, for example, using a neck-like connection nozzle mounted on the transducer housing 100. Within the connection nozzle can be arranged, furthermore, a hermetically sealed and/or pressure resistant feedthrough, for example, a feedthrough formed by means of glass—and/ or plastic potting compound, for electrical connecting lines between electrical components of the measuring transducer MT and the electronics ME.

The measuring system according to the invention is, furthermore, adapted, consequently the method implemented therewith for measuring the density according to the invention is, furthermore, so constructed, that, for ascertaining the density measured value $X_\rho$, besides the at least one parameter measured value representing the wanted frequency of the at least one oscillation measurement signal s1, supplementally also a tilt measured value $X_\gamma$, namely a measured value for an inclination of the at least one measuring tube in the static resting position relative to a local acceleration of gravity amounting, for example, to 9.8 m·s$^{-2}$, respectively applied with 9.8 m·s$^{-2}$, is ascertained and caused to enter into the calculating of the density measured value, in such a manner that both the at least one parameter measured value as well as also the tilt measured value are used for ascertaining at least one density measured value $X_\rho$ representing the density of the fluid. The tilt measured value $X_\gamma$ is so determined according to the invention that it represents, as, for example, also correspondingly illustrated in FIGS. 4, 5 and 6, an angle of intersection γ between a direction vector $e_y$ of an imaginary first reference axis y (y-axis) and a direction vector $e_g$ of an imaginary second reference axis g (g-axis). The first reference axis is, in such case, so selected that it is perpendicular to an imaginary third reference axis z (z-axis) imaginarily connecting the first tube end and the second tube end, and that it points in the direction of a peak of the at least one measuring tube most remote from the third reference axis z in the static resting position. The above mentioned second reference axis g, in turn, extends through a shared intersection of the first and third reference axes and points in the vertical direction ($e_g$=g/g), namely in direction of the local acceleration of gravity g. The angle of intersection γ can, in such case, lie in the interval from 0° to 180°, consequently is greater than 0° and less than 180°. In an additional embodiment of the invention, a component, for example, thus a coil or a permanent magnet, of the above described electro-mechanical oscillation exciter useful for the active exciting of oscillations of the at least one measuring tube is so placed on the at least one measuring tube that the imaginary first reference axis, or a lengthening thereof, imaginarily intersects the oscillation exciter, i.e. the component of the oscillation exciter.

By ascertaining and applying the above discussed tilt measured value, it becomes possible to take into consideration, and appropriately to correct, a dependence of the signal parameter on the inclination of the at least one measuring tube, as well as also a total weight of the measuring tube with fluid located therein, in the case of ascertaining the density, namely a dependence in the form of a deformation of the at least one measuring tube dependent on this inclination, i.e. the angle by intersection γ, under the influence of the force by gravity acting thereon. The tilt measured value $X_\gamma$ can, for example, be so ascertained for this that it corresponds to a numerical value related to angular degrees for the angle of intersection, for example, thus to a formula containing a scalar product $e_y \circ e_g$ (inner product or dot product) of the two direction vectors $e_y$, $e_g$:

$$\cos X_\gamma = \frac{e_y \circ e_g}{|e_y| \cdot |e_g|} \tag{1}$$

or that the tilt measured value $X_\gamma$ corresponds to a numerical value for a cosine of the angle of intersection, for example, thus according to the formula:

$$X_\gamma = \frac{e_y \circ e_g}{|e_y| \cdot |e_g|} \tag{2}$$

Accordingly, in an additional embodiment of the invention, the ascertaining of the tilt measured value, consequently the ascertaining of the density measured value, comprises ascertaining a cosine, cos γ, of the angle of intersection γ, or ascertaining the angle of intersection in angular degrees.

By taking into consideration an additional imaginary axis, namely an imaginary fourth reference axis x (x-axis), which is both perpendicular to the imaginary reference axis y (y-axis) as well as also perpendicular to the imaginary reference axis z (z-axis), that is, a direction vector $e_x$ of the reference axis x, the angle of intersection γ can, furthermore, also be ascertained based on a formula:

$$\cos X_\gamma = \frac{e_z \circ e_h}{|e_z| \cdot |e_h|} \cdot \frac{e_y \circ e_v}{|e_y| \cdot |e_v|} \tag{3}$$

or a formula:

$$X_\gamma = \frac{e_z \circ e_h}{|e_z| \cdot |e_h|} \cdot \frac{e_y \circ e_v}{|e_y| \cdot |e_v|} \tag{4}$$

wherein a direction vector $e_h$ corresponds to a formula containing a cross product $e_z \times e_g$ (outer product) of the two direction vectors $e_z$, $e_g$:

$$e_h = \frac{e_g \times (e_z \times e_g)}{|e_g \times (e_z \times e_g)|} = \frac{e_g \times (e_z \times e_g)}{|e_g| \cdot |e_z \times e_g|} \tag{5}$$

consequently a rotation of the imaginary second reference axis g by −90° within an imaginary projection plane (gz) imaginarily defined by the reference axis g and the imaginary third reference axis z, respectively a rotation of the reference axis g in the projection plane into a horizontal position, and a directional vector $e_v$ is defined by a formula $$e_v = \frac{e_g \circ e_x}{|e_x|^2} \cdot e_x + \frac{e_g \circ e_y}{|e_y|^2} \cdot e_y \tag{6}$$

consequently an orthogonal projection of the second reference axis g onto an imaginary projection plane (xy) imaginarily defined by the imaginary first reference axis y and the imaginary fourth reference axis x. Accordingly, the sought angle of intersection γ, or the tilt measured value $X_\gamma$ representing such, can, for example, also be calculated as a product of a cosine of an angle of intersection η (cos η) between the direction vector $e_z$ of the imaginary third reference axis z and the previously indicated direction vector $e_h$ defined by the position of the imaginary third reference axis z relative to the second reference axis g multiplied by a cosine of an angle of intersection ζ (cos ζ) between the direction vector $e_y$ of the imaginary first reference axis y and the previously indicated direction vector $e_v$ defined by the position of the imaginary first and fourth reference axes relative to the imaginary second reference axis g (cos γ=cos η·cos ζ).

The tilt measured value can be ascertained and correspondingly furnished in the electronics, in given cases, also on the part of the manufacturer of the measuring system, for example, based on planning documents establishing the above discussed, installed position. Alternatively or supplementally, the ascertaining of the tilt measured value can, however, also involve a measuring of the angle of intersection, for example, namely a measuring on-site after the measuring transducer has been placed in its final installed position, consequently the at least one measuring tube is in its static resting position. The measuring of the angle of intersection can then be accomplished, for example, by means of an inclinometer, for instance, by placing the inclinometer, for example, an electronic, for instance digital, inclinometer, externally on the measuring transducer housing 100, for instance on reference marking provided therefor to represent the reference axis y axis (y-axis) and/or the reference axes x, y, or, such as a e.g. provided in WO-A 2013/092105, temporarily securing the inclinometer on the electronics housing and at the same time connecting it with the electronics, for example, via a service interface, in given cases, provided in the electronics. A numerical value ascertained by means of the inclinometer for the measured inclination, or the orientation measured for the particular reference axis can, in each case, be thereafter appropriately transmitted to the electronics, for example, by manual input via display—and interaction element HMI, or by data transmission via communication circuit COM or via the above mentioned service interface. Alternatively or supplementally, the measuring system can, however, for example, also be equipped with its own inclination sensor 61, which is arranged in the measuring system, for example, namely within the electronics housing 200 or also within the measuring transducer housing 100 or, however, for example, also within the connection nozzle, and electrically coupled with the electronics to form an "on-board" inclinometer, and, accordingly, the ascertaining of the tilt measured value can occur with application of the inclination sensor 71. The inclination sensor 71 —, for example, also one already delivering a sensor signal representing the cosine $\cos \gamma$ of the angle of intersection $\gamma$, or digital measured values representing the cosine $\cos \gamma$ of the angle of intersection $\gamma$—can in advantageous manner be so secured that it is durably positioned in a fixed relationship relative to the at least one measuring tube 10, consequently relative to the first and third reference axes, for instance, in such a manner that a measurement axis of the inclination sensor 71 is parallel to the first reference axis (y-axis), or coincides with the first reference axis (y-axis). The inclination sensor 71 can be, for example, a uniaxial inclination sensor, namely one having exactly one measurement axis; equally as well, the inclination sensor 71 can, however, also have two or more measurement axes perpendicular to one another. In the case of installed measuring system—not least of all one with an installed position, for instance, corresponding, or comparable, to the installed position shown in FIG. 6—the actual orientation of the direction vectors $e_h$ and $e_v$ can, at times, not least of all in the case without an electronic inclination sensor, or without an on-board inclinometer, simply be ascertained as the position of the reference axis y. Accordingly, the ascertaining of the inclination value on-site can, at times, also be accomplished by, first of all, ascertaining the two angles of intersection $\eta$, $\zeta$ and inputting such into the electronics of the measuring system, for example, via display—and interacting element HMI, and thereafter calculating by means of the electronics the sought angle of intersection $\gamma$, or the tilt measured value $X_\gamma$, based on one of the previously discussed formulas (3), or (4), and based on the two angles of intersection $\eta$, $\zeta$.

The tilt measured value $X_\gamma$—however ascertained—can in advantageous manner, furthermore, be stored in a data memory provided, in given cases, in the electronics ME, for example, also durably in the above mentioned non-volatile data memory (EEPROM) of the electronics ME. In this way, it is, for example, also enabled to ascertain the tilt measured value $X_\gamma$ earlier, for instance, on-site in the course of a start-up of the respective measuring device, and thereafter, by reading the tilt measured value from the data memory, to use the read-out value for ascertaining the density measured value $X_\rho$. The ascertaining of the tilt measured value $X_\gamma$ and the permitting of the fluid to flow through the at least one measuring tube, as well as also the ascertaining of the tilt measured value $X_\gamma$ and the causing of the at least one measuring tube to vibrate can, in such case, occur immediately, however, thus, in each case, at the same time, so that the tilt measured value $X_\gamma$ can be ascertained, even recurringly, during operation of the measuring system.

The ascertaining of the density can occur, for example, in such a manner that, first of all, a provisional density measured value $X_{\rho\_prov}$ is ascertained, which only interim represents the density of the fluid and the provisional density measured value $X_{\rho\_prov}$ and which is thereafter recurringly converted during operation of the measuring system into the updated density measured value $X_\rho$ with application of a tilt correction value $X_{korr}$ ascertained based on the tilt measured value $X_\gamma$, wherein the tilt correction value $X_{korr}$ represents a dependence $Err_f$ of the signal parameter both on the inclination of the at least one measuring tube, for example, namely on a cosine of the angle of intersection, as well as also on a total weight of the at least one measuring tube with fluid located therein, respectively a measuring error resulting therefrom in the provisional density measured value $X_{\rho\_prov}$. The provisional density measured value $X_{\rho\_prov}$ and the tilt correction value $X_{korr}$ can, for example, be so calculated that with them the density measured value thereafter results in simple manner based on a formula:

$$X_\rho = X_{\rho\_prov} + X_{korr}, \qquad (7)$$

so that a formula containing a term:

$$c_0 + \frac{c_1}{X_f^2} + X_{korr} \qquad (8)$$

can be ascertained. The above mentioned provisional density measured value $X_{\rho\_prov}$ can, in turn, be, for example, a conventionally ascertained density measured value, for example, thus a density measured value, which in the case of an angle of intersection of 0° represents density, which is actually less than the density of the fluid, or which in the case of an angle of intersection of 180° represents density, which is greater than the density of the fluid, for example, thus be ascertained with application of a formula containing a term $$X_{\rho\_prov} = c_0 + \frac{c_1}{X_f^2} \qquad (9)$$

The provisional density measured value $X_{\rho\_prov}$ can in advantageous manner additionally be so calculated, or the measuring system specific coefficients $c_0$, $c_1$ contained in the previously indicated formula, consequently coefficients earlier ascertainable, for instance, in the course of a calibration, can in advantageous manner also be so selected that—at least at a reference temperature predetermined for the fluid—the provisional density measured value and the density measured value are equal at an angle of intersection of 90°. The tilt correction value $X_{korr}$ ascertained for the purpose of correction of the provisional density measured value $X_{\rho\_prov}$ can, for instance, for the case, in which the tilt measured value $X_\gamma$ corresponds to a numerical value related to angular degrees for the angle of intersection $\gamma$, for example, occur based on a formula containing a term:

$$X_{korr} \sim \frac{\cos X_\gamma}{X_f^4} \tag{10}$$

or a term:

$$X_{korr} = c_{10,I} \cdot g \cdot \frac{\cos X_\gamma}{X_f^4} = c^*_{10,I} \cdot \frac{\cos X_\gamma}{X_f^4} \tag{11}$$

For the other case, in which the tilt measured value $X_\gamma$ corresponds to a cosine of the angle of intersection $\gamma$, the tilt correction value $X_{korr}$ can be ascertained, for example, also based on a formula containing a term:

$$X_{korr} \sim \frac{X_\gamma}{X_f^4} \tag{12}$$

or a term:

$$X_{korr} = c_{10,I} \cdot g \cdot \frac{X_\gamma}{X_f^4} = c^*_{10,I} \cdot \frac{X_\gamma}{X_f^4} \tag{13}$$

wherein the measuring system specific coefficients $c_{10,I}$, respectively $c^*_{10,I}$, can, again, be ascertained earlier, for instance, in the course of a calibration, namely by calibrating the respective measuring system under reference conditions.

As directly evident from these formulas, the ascertaining of the density measured value, for example, also the ascertaining of the previously indicated tilt correction value $X_{korr}$, can, among other things, also include a recurring ascertaining of a square $f_N^2$ of the wanted oscillation frequency $f_N$ of the at least one measuring tube and/or a recurring ascertaining of a fourth power $f_N^4$ of the wanted oscillation frequency $f_N$ of the at least one measuring tube. The square $f_N^2$ of the wanted oscillation frequency $f_N$, or the fourth power $f_N^4$, of the wanted oscillation frequency $f_N$ can, for example, be calculated, in each case, also with application of the at least one parameter measured value $X_f$.

Alternatively to the above discussed application of a provisional, equally as well defective, density measured value, and a subsequent correction of the provisional density measured value, the density measured value can, furthermore, however, for example, also be ascertained directly based on the parameter measured value $X_f$ and the tilt measured value $X_\gamma$, respectively a tilt correction value $X_{korr}$ derived in the meantime therefrom, for example, namely in such a manner that the ascertaining of the density measured value comprises ascertaining a square $f_N^2$ of the wanted oscillation frequency $f_N$ of the at least one measuring tube, reduced by the tilt correction value $X_{korr}$, for instance based on a formula containing a term:

$$c_0 + \frac{c_1}{X_f^2 - X_{korr}} \tag{14}$$

This variant brings, among other things, also the advantage that the tilt correction value $X_{korr}$ is describable as a function of the tilt measured value $X_\gamma$ and is established for the particular measuring system just by knowledge of the tilt measured value $X_\gamma$, especially in such a manner that, for the case, in which the tilt measured value $X_\gamma$ corresponds to a numerical value for the angle of intersection $\gamma$ related to angular degrees, the following formula holds for the tilt correction value $X_{korr}$:

$$X_{korr} = c_{10,II} \cdot g \cdot \cos X_\gamma = c^*_{10,II} \cdot \cos X \sim \cos X_\gamma \tag{15}$$

or for the other the case, in which the tilt measured value $X_\gamma$ corresponds to a cosine of the angle of intersection $\gamma$, the following formula holds for the tilt correction value $X_{korr}$:

$$X_{korr} = c_{10,II} \cdot g \cdot X_\gamma = c^*_{10,II} \cdot X_\gamma \sim X_\gamma \tag{16}$$

so that the tilt correction value $X_{korr}$ can be calculated accordingly. As a result of this, also the tilt correction value $X_{korr}$ can, same as the tilt measured value $X_\gamma$, already be suitably ascertained at start-up of the respective measuring system and stored as a constant in the respective electronics ME, for example, namely in the previously mentioned non-volatile data memory EEPROM, in order thereafter to be able to be read-out for ascertaining the density measured value.

The invention claimed is:

1. Method for measuring density of a fluid by means of at least one at least sectionally curved, measuring tube, which is adapted to be flowed through by the fluid and concurrently to be caused to vibrate over a wanted oscillatory length, namely a tube length measured from a first tube end to a second tube end, which is greater than a minimum separation of the second tube end from the first tube end, which method comprises:
   ascertaining a tilt measured value, $X_\gamma$, namely a measured value for an inclination of the at least one measuring tube in static resting position relative to a local acceleration of gravity, in such a manner that the tilt measured value, $X_\gamma$, represents an angle of intersection, $\gamma$, between a direction vector, $e_y$, of an imaginary first reference axis (y-axis) and a direction vector, $e_g$, of an imaginary second reference axis (g-axis),
   wherein the first reference axis is perpendicular to an imaginary third reference axis (z-axis) imaginarily connecting the first tube end and the second tube end, and points in the direction of a peak of the at least one measuring tube farthest from the third reference axis (z-axis) in the static resting position, and
   wherein the second reference axis extends through a shared intersection of the first and third reference axes and points in the vertical direction ($e_g=g/g$), namely in the direction of the local acceleration of gravity, g;
   permitting fluid to flow through the at least one measuring tube and causing the measuring tube to vibrate, in such a manner that the at least one measuring tube executes, at least partially, wanted oscillations with a wanted oscillation frequency, $f_N$, dependent on the density of the fluid;
   producing at least one oscillation signal (s1) representing at least oscillations of the at least one measuring tube, in such a manner that the oscillation signal has at least one signal parameter corresponding to the wanted oscillation frequency, $f_N$;
   using the at least one oscillation signal (s1) for ascertaining at least one parameter measured value, $X_f$, for the signal parameter, in such a manner that the parameter measured value represents the wanted oscillation frequency, $f_N$, of the at least one measuring tube; and
using both the at least one parameter measured value as well as also the tilt measured value for ascertaining at least one density measured value, $X_\rho$, representing the density of the fluid.

2. Method as claimed in claim 1, further comprising: bringing the at least one measuring tube into a static resting position.

3. Method as claimed in claim 1, wherein the ascertaining of the density measured value comprises ascertaining a cosine, $\cos\gamma$, of the angle of intersection, $\gamma$.

4. Method as claimed in claim 1, wherein the ascertaining of the density measured value comprises ascertaining a square, $f_N^2$, of the wanted oscillation frequency, $f_N$, of the at least one measuring tube.

5. Method as claimed in claim 1, wherein the ascertaining of the density measured value comprises using the at least one parameter measured value for ascertaining a square, $f_N^2$, of the wanted oscillation frequency, $f_N$, of the at least one measuring tube.

6. Method as claimed in claim 1, wherein the ascertaining of the at least one density measured value comprises using both the at least one parameter measured value as well as also the tilt measured value for ascertaining a tilt correction value $X_{korr}$.

7. Method as claimed in claim 6, wherein a formula for ascertaining the density measured value contains a term, $$c_0 + \frac{c_1}{X_f^2} + X_{korr}.$$

8. Method as claimed in claim 6, wherein the ascertaining of the tilt correction value, $X_{korr}$, comprises ascertaining a square, $f_N^2$, of the wanted oscillation frequency, $f_N$, of the at least one measuring tube.

9. Method as claimed in claim 6, wherein the ascertaining of the tilt correction value, $X_{korr}$, comprises using the at least one parameter measured value for ascertaining a square, $f_N^2$, of the wanted oscillation frequency, $f_N$, of the at least one measuring tube.

10. Method as claimed in claim 6, wherein the ascertaining of the tilt correction value, $X_{korr}$, comprises ascertaining a fourth power, $f_N^4$, of the wanted oscillation frequency, $f_N$, of the at least one measuring tube.

11. Method as claimed in claim 6, wherein the ascertaining of the tilt correction value, $X_{korr}$, comprises using the at least one parameter measured value for ascertaining a fourth power, $f_N^4$, of the wanted oscillation frequency, $f_N$, of the at least one measuring tube.

12. Method as claimed in claim 6, wherein the tilt correction value, $X_{korr}$, satisfies a formula:

$$X_{korr} \sim \frac{\cos X_\gamma}{X_f^4},$$

or a formula:

$$X_{korr} = c_{10,I} \cdot g \cdot \frac{\cos X_\gamma}{X_f^4} = c_{10,I}^* \cdot \frac{\cos X_\gamma}{X_f^4}.$$

13. Method as claimed in claim 6, wherein the tilt correction value, $X_{korr}$, satisfies a formula:

$$X_{korr} \sim \frac{X_\gamma}{X_f^4},$$

or a formula:

$$X_{korr} = c_{10,I} \cdot g \cdot \frac{X_\gamma}{X_f^4} = c_{10,I}^* \cdot \frac{X_\gamma}{X_f^4}.$$

14. Method as claimed in claim 6, wherein the ascertaining of the density measured value comprises ascertaining a provisional density measured value, $X_{\rho\_prov}$, which represents, interim, the density of the fluid.

15. Method as claimed in claim 14, wherein the provisional density measured value in the case of an angle of intersection of 0° represents density, which is less than the density of the fluid.

16. Method as claimed in claim 14, wherein the provisional density measured value in the case of an angle of intersection of 180° represents density, which is greater than the density of the fluid.

17. Method as claimed in claim 14, wherein the provisional density measured value and the density measured value are equal in the case of an angle of intersection of 90°.

18. Method as claimed in claim 14, wherein a formula for ascertaining the provisional density measured value contains a term, $$X_{\rho\_prov} = c_0 + \frac{c_1}{X_f^2}.$$

19. Method as claimed in claim 14, wherein a formula for ascertaining the density measured value contains a term, $X_{\rho\_prov} + X_{korr}$.

20. Method as claimed in claim 6, wherein the tilt correction value, $X_{korr}$, satisfies a formula:

$$X_{korr} \sim \cos X_\gamma$$

or a formula:

$$X_{korr} = c_{10,II} \cdot g \cdot \cos X_\gamma = c_{10,II}^* \cdot \cos X_\gamma.$$

21. Method as claimed in claim 20, wherein the ascertaining of the density measured value comprises ascertaining a square, $f_N^2$, of the wanted oscillation frequency, $f_N$, of the at least one measuring tube, reduced by the tilt correction value, $X_{korr}$.

22. Method as claimed in claim 6, wherein the tilt correction value, $X_{korr}$, satisfies a formula:

$$X_{korr} \sim X_\gamma,$$

or a formula:

$$X_{korr} = c_{10,II} \cdot g \cdot X_\gamma = c_{10,II}^* \cdot X_\gamma.$$

23. Method as claimed in claim 6, further comprising: storing the tilt correction value, $X_{korr}$, in a data memory.

24. Method as claimed in claim 23, wherein use of the tilt correction value, $X_{korr}$, for ascertaining the density measured value, $X_\rho$, comprises reading the tilt correction value, $X_{korr}$, from the data memory.

25. Method as claimed in claim 1, wherein a formula for ascertaining the density measured value contains a term, $$c_0 + \frac{c_1}{X_f^2 - c_{10,u} \cdot g \cdot \cos X_Y},$$

or a term, $$c_0 + \frac{c_1}{X_f^2 - c_{10,u} \cdot g \cdot X_Y}.$$

26. Method as claimed in claim 1, further comprising: storing the tilt measured value, $X_\gamma$, in a data memory.

27. Method as claimed in claim 26, wherein using the tilt measured value for ascertaining the density measured value, $X_\rho$, comprises reading the tilt measured value from the data memory (EEPROM).

28. Method as claimed in claim 1, wherein the ascertaining of the tilt measured value, $X_\gamma$, comprises measuring the angle of intersection.

29. Method as claimed in claim 1, wherein the ascertaining of the tilt measured value, $X_\gamma$, comprises ascertaining a cosine of the angle of intersection.

30. Method as claimed in claim 1,
wherein the tilt measured value, $X_\gamma$, corresponds to a numerical value for the angle of intersection; and/or
wherein the tilt measured value, $X_\gamma$, satisfies a formula:

$$\cos X_Y = \frac{e_y \circ e_g}{|e_y| \cdot |e_g|};$$

and/or
wherein the tilt measured value, $X_\gamma$, satisfies a formula:

$$\cos X_Y = \frac{e_z \circ e_h}{|e_z| \cdot |e_h|} \cdot \frac{e_y \circ e_v}{|e_y| \cdot |e_v|}$$

wherein a direction vector $e_h$ satisfies a formula:

$$e_h = \frac{e_g \times (e_z \times e_g)}{|e_g \times (e_z \times e_g)|} = \frac{e_g \times (e_z \times e_g)}{|e_g| \cdot |e_z \times e_g|}$$

and a direction vector $e_V$ satisfies a formula containing a direction vector, $e_x$, of an imaginary fourth reference axis x (x-axis):

$$e_v = \frac{e_g \circ e_x}{|e_x|^2} \cdot e_x + \frac{e_g \circ e_y}{|e_y|^2} \cdot e_y,$$

wherein the imaginary fourth reference axis x is both perpendicular to the imaginary first reference axis (y-axis) as well as also perpendicular to the imaginary third reference axis (z-axis).

31. Method as claimed in claim 1,
wherein the tilt measured value, $X_\gamma$, corresponds to a numerical value for a cosine of the angle of intersection; and/or
wherein the tilt measured value, $X_\gamma$, satisfies a formula:

$$X_Y = \frac{e_y \circ e_g}{|e_y| \cdot |e_g|};$$

and/or
wherein the tilt measured value, $X_\gamma$, satisfies a formula:

$$X_Y = \frac{e_z \circ e_h}{|e_z| \cdot |e_h|} \cdot \frac{e_y \circ e_v}{|e_y| \cdot |e_v|},$$

wherein a direction vector $e_h$ satisfies a formula:

$$e_h = \frac{e_g \times (e_z \times e_g)}{|e_g \times (e_z \times e_g)|} = \frac{e_g \times (e_z \times e_g)}{|e_g| \cdot |e_z \times e_g|}$$

and a direction vector $e_V$ satisfies a formula containing a direction vector, $e_x$, of an imaginary fourth reference axis x (x-axis):

$$e_v = \frac{e_g \circ e_x}{|e_x|^2} \cdot e_x + \frac{e_g \circ e_y}{|e_y|^2} \cdot e_y,$$

wherein the imaginary fourth reference axis x is both perpendicular to the imaginary first reference axis (y-axis) as well as also perpendicular to the imaginary third reference axis (z-axis).

32. Method as claimed in claim 1, wherein the ascertaining of the tilt measured value, $X_\gamma$, and the permitting of fluid to flow through the at least one measuring tube occur at the same time.

33. Method as claimed in claim 1, wherein the ascertaining of the tilt measured value, $X_\gamma$, and the causing of the at least one measuring tube to vibrate occur at the same time.

34. Method as claimed in claim 1, further comprising: using an inclination sensor.

35. Method as claimed in claim 34,
wherein the inclination sensor has two or more measurement axes perpendicular to one another; and/or
wherein the inclination sensor is so arranged that a measurement axis is parallel to the first reference axis (y-axis).

36. Method as claimed in claim 34, wherein the inclination sensor is held durably in a fixed positional relationship relative to the at least one measuring tube, consequently relative to the first and third reference axes.

37. Method as claimed in claim 1, wherein the at least one measuring tube has only two oscillation nodes, of which a first oscillation node is located in the first tube end and a second oscillation node is located in the second tube end, and, consequently, the at least one measuring tube has a bending oscillation fundamental mode having a single oscillatory antinode.

38. Method as claimed in claim 37, wherein the wanted oscillations of the at least one measuring tube correspond to the bending oscillation fundamental mode.

39. Method as claimed in claim 1, wherein on the at least one measuring tube a component useful for active exciting of oscillations of the measuring tube, is placed, in such a manner that the imaginary first reference axis imaginarily intersects the oscillation exciter, or the component of the oscillation exciter.

* * * * *